United States Patent [19]

Gray

[11] Patent Number: 4,510,924

[45] Date of Patent: Apr. 16, 1985

[54] BRACHYTHERAPY DEVICES AND METHODS EMPLOYING AMERICIUM-241

[75] Inventor: Laurence A. Gray, New Haven, Conn.

[73] Assignee: Yale-New Haven Hospital, Inc., New Haven, Conn.

[21] Appl. No.: 457,731

[22] Filed: Jan. 13, 1983

Related U.S. Application Data

[63] Continuation of Ser. No. 168,270, Jul. 10, 1980, abandoned, which is a continuation of Ser. No. 157,057, Jun. 6, 1980, abandoned.

[51] Int. Cl.³ .............................................. A61N 5/00
[52] U.S. Cl. ...................................... 128/1.2; 424/1.1
[58] Field of Search ...................... 128/1.1, 1.2; 424/1

[56] References Cited

U.S. PATENT DOCUMENTS 3,488,502  1/1970  Dukes ................................. 250/106

Primary Examiner—Kyle L. Howell
Assistant Examiner—John C. Hanley
Attorney, Agent, or Firm—Kerkam, Stowell, Kondracki & Clarke

[57] ABSTRACT

Sources and methods for radiation therapy, particularly brachytherapy, employing americium-241 radioisotope. The physical properties of americium-241 (60 keV gamma emission and 433 year half-life) provide major advantages for radiotherapy, including simplified radiation protection, dose reduction to healthy tissue, increased dose to tumor, and improved dose distributions. A number of apparent drawbacks and unfavorable considerations including low gamma factor, high self-absorption, increased activity required and alpha-particle generation leading to helium gas pressure buildup and potential neutron contamination in the generated radiation are all effectively dealt with and overcome through recognition of subtle favorable factors unique to americium-241 among brachytherapy sources and through suitable constructional techniques. Due to an additional amount of radiation, in the order of 50%, provided primarily to nearby regions as a result of Compton scatter in tissue and water, higher dose rates occur than would be predicted by conventional calculations.

9 Claims, 19 Drawing Figures

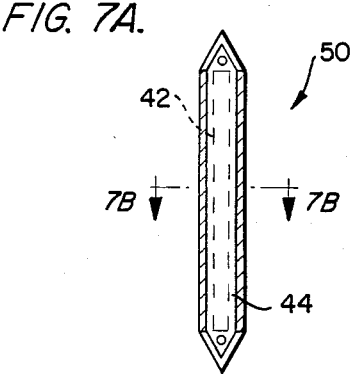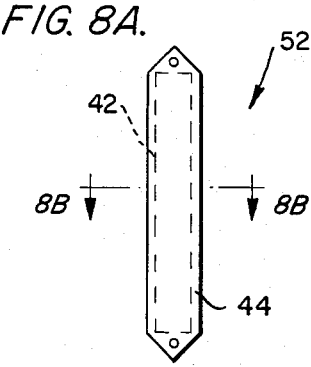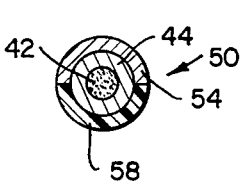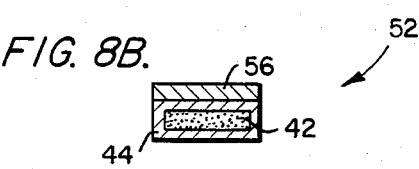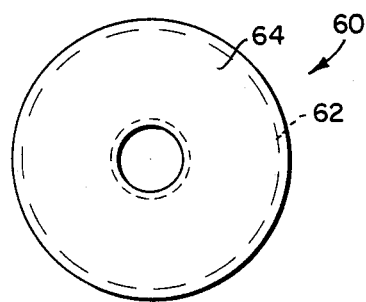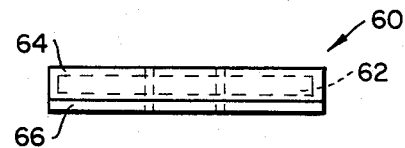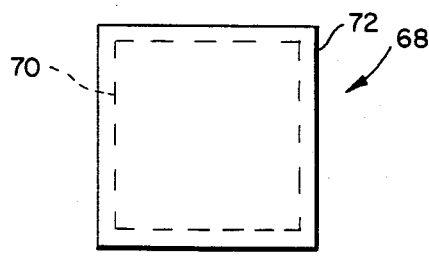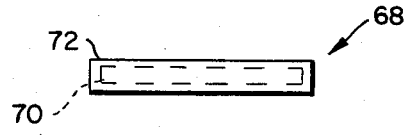

BRACHYTHERAPY DEVICES AND METHODS EMPLOYING AMERICIUM-241

CROSS-REFERENCE TO RELATED APPLICATIONS

This is a continuation of copending application Ser. No. 168,270, filed July 10, 1980, and now abandoned, in turn a continuation-in-part of then-copending application Ser. No. 157,057, filed June 6, 1980, now abandoned.

BACKGROUND OF THE INVENTION

The present invention relates generally to therapeutic radiology and, more particularly, to devices and methods for brachytherapy.

As is known, radiation therapy refers to the treatment of diseases with radiation. Of particular interest is the treatment of tumors, including malignant tumors such as cancer. In radiation therapy, it is desired to destroy the malignant tissue while minimizing the exposure of medical personnel to radiation and minimizing radiation damage to other tissue, such as nearby healthy tissue.

"Brachytherapy", with which the present invention is particularly concerned, is such treatment at relatively short distances, typically 0–3 cm, between the radioactive source and the relevant tissue. "Brachytherapy" is a comprehensive term including therapy effected by interstitial, intercavitary, and surface applicators. Interstitial and intracavitary techniques are particularly advantageous where superficial or accessible diseased tissue is involved. In contrast, another form of radiation therapy, "external beam therapy", involves treatment at relatively large distances, e.g. 70–100 cm between the radiation source and the skin. With "external beam therapy" it is difficult to minimize damage to underlying normal tissues.

There are two general types of brachytherapy, respectively involving permanent implants and temporary implants. By way of example, for permanent implants radioactive seeds containing radon and iodine-125 have been employed. For temporary implants, radium, cesium-137, and iridium-192 have been employed.

The foregoing provides a very brief summary of the context of the present invention. However, it is believed that the significant advance of the present invention will be better appreciated in light of an historical summary, as follows:

A wide variety of radioactive elements (radioisotopes) have been proposed for therapeutic use. Only a relatively small number have actually been accepted and employed on a large scale basis. This is due at least in part to a relatively large number of constraining considerations where medical treatment is involved. Important considerations are gamma ray energy, half-life, and availability.

An element employed almost immediately after its discovery in 1898, and one which is still in common use despite certain highly undesirable properties, is radium. By way of example, the following U.S. patents are cited for their disclosures of the use of radium in radiotherapy: Heublein U.S. Pat. No. 1,626,338; Clayton U.S. Pat. No. 2,959,166; and Rush U.S. Pat. No. 3,060,924.

A significant advantage in the use of radium for many purposes is its relatively long half-life, which is approximately 1600 years. The significance of a long half-life is that the quantity of radiation emitted by a particular sample remains essentially constant over a long period of time. Thus, a therapeutic source employing radium may be calibrated in terms of its dose rate, and will remain essentially constant for many years. Not only does this simplify dosage calculation, but long term cost is reduced because the source need not be periodically replaced.

However, a particularly undesirable property of radium is the requirement for careful attention to the protection of medical personnel, as well as healthy tissue of the patient. This is due to its complex and highly penetrating gamma ray emission, for example a component at 2440 keV. To minimize exposure to medical personnel, specialized and sometimes complicated "after loading" techniques have been developed whereby the radioisotope is guided, for example through a hollow tube, to the treatment region following the preliminary emplacement of the specialized appliances required.

In the past decade, cesium-137, despite a half-life of only 27 years, much shorter than that of radium, has gradually been displacing radium for the purpose of brachytherapy, especially intracavitary radiotherapy. Gamma radiation from cesium-137 is at a level of 660 keV compared to 2440 keV for the highest energy component of the many emitted by radium. This lower gamma energy has enabled radiation shielding to become more manageable, and is consistent with the recent introduction of the "as low as is reasonably achievable" (ALARA) philosophy for medical institutions. By way of example, the following U.S. patents are cited for their disclosures of the use of cesium-137 for radiotherapy: Simon U.S. Pat. No. 3,750,653; Chassagne et al U.S. Pat. No. 3,861,380; and Clayton U.S. Pat. No. 3,872,856. The Rush U.S. Pat. No. 3,060,924, referred to above for its disclosure of a radium source, also discloses the use of cesium-137.

Even more recently, the radioisotope iodine-125 has been employed for radiotherapy, particularly for permanent implants. A representative disclosure may be found in the Lawrence U.S. Pat. No. 3,351,049. Iodine-125, as well as other radioisotopes disclosed in the Lawrence U.S. Pat. No. 3,351,049, differ significantly from previously employed radioisotopes such as radium and cesium-137 in that the energy level of its gamma radiation is significantly lower. For example, iodine-125 emits gamma rays at a peak energy of 35 keV. Other radioisotopes disclosed in the Lawrence U.S. Pat. No. 3,351,049 are cesium-131 and palladium-103, which generate gamma radiation at 30 keV and 40 keV, respectively. Radioisotopes having similar properties are also disclosed in the Packer et al U.S. Pat. No. 3,438,365. Packer et al suggest the use of Xenon-133, which emits gamma rays at 81 keV, and Xenon-131, which generates gamma radiation at 164 keV.

Experience with such low energy gamma sources in radiotherapy has demonstrated that very low energy gamma rays, as low as 35 keV, can be highly effective for permanent implants. Significantly, such low gamma ray energy levels drastically simplify radiation shielding problems, reducing shielding problems to a level comparable to that of routine diagnostic radiology.

However, along with gamma ray energy, another physical property of such radioisotopes which must be considered is half-life. As briefly discussed above, a long half-life is desirable in many respects, especially when such factors as dosage calculation and long term cost are considered. The low energy gamma emitters mentioned above, as well as various others heretofore proposed and employed, share the common property of relatively short half-life. For example, the half-life of iodine-125 is 60 days, and the half-lives of paladium-103 and cesium-131 are only 17 and 10 days respectively. The half-life of xenon-133 is approximately 5 days and that of xenon-131, 12 days.

(There is no intention herein to suggest that such radioisotopes with relatively short half-lives are not therapeutically useful. In fact, the contrary is true. As the various references identified above point out, a short half-life is essential for permanent implants. Such radioisotopes may be more or less permanently implanted or embedded in a patient, for example, interstitially, and will deliver a calculable radiation dose over a predictable period of time, after which the radiation decays to a relatively insignificant level.)

For other than permanent implants, such low energy gamma emitting radioisotopes have a number of drawbacks related to convenience of use. In particular, with the radiation level rapidly decaying, shelf life becomes an important consideration. In order to achieve a desired dosage level, the time of radioactive sample preparation relative to the time of therapy must be carefully controlled, with attendant complexity. Further, such sources must be frequently replenished, requiring a continuing expenditure.

Because of these drawbacks relating to short half-life, the use of low energy radioisotopes such as iodine-125 and radon is currently limited to permanent implants. In short, the now-recognized advantages from the standpoints of shielding and radiation control possible with low energy gamma emmitters have been outweighed by the drawbacks attendant to short half-life.

SUMMARY OF THE INVENTION

The present invention provides radiation sources for brachytherapy and methods for radiation therapy employing a radioisotope which combines the advantages of very low energy and long half-life, and which is readily available at reasonable cost. Several major advantages for radiotherapy are provided.

Briefly stated, and in accordance with an overall concept of the invention, it is recognized and appreciated that the radioisotope americium-241, which has not heretofore been employed in such applications, possesses a number of desirable properties leading to potential major advantages. However, americium-241 also has a number of undesirable properties. In accordance with the present invention, it is recognized that these undesirable properties may be minimized to such an extent that the advantages far outweigh the disadvantages for radiotherapy, particularly brachytherapy, applications.

In particular, advantageous physical properties of americium-241 radioisotope are very low energy gamma radiation at 60 keV (38.4% efficiency), and a relatively long half-life of 433 years. Americium-241 is a byproduct of nuclear fission, readily available at reasonable cost. Thus, a substantially permanent source of low energy of gamma radiation for brachytherapy purposes can be provided.

It is believed that, out of more than one thousand known radioisotopes, americium-241 is unique in that it offers the advantageous physical properties of low gamma radiation energy and long half-life, and at the same time is readily commercially available. The current price of americium-241 is approximately $235/Ci. While this may lead to higher initial costs than a cesium-137 system, the stock does not have to be replaced routinely and is a "one-time" purchase for an institution.

However, there are a number of selection considerations and drawbacks which, when conventional selection approaches are taken, lead to the conclusion that americium-241 would be entirely unsuitable for brachytherapy purposes. These are discussed next below for the purpose of setting forth likely reasons why americium-241 has not previously been proposed for brachytherapy purposes, and in fact has heretofore been overlooked.

Important selection considerations relate to radiation exposure rate and quantity requirements. In this art, the "amount" of a radioactive isotope is more conveniently stated as "activity." The special unit of activity is the curie (Ci), or the lesser millicurie (mCi). Although it is not possible to actually count the atoms present, it is easy to count the quantity of radiation emitted. By definition, a curie (Ci) is a unit quantity in which $3.7 \times 10^{10}$ disintegrations occur per second. Typical cesium-137 brachytherapy sources are 25–60 mCi each, and typical radium sources are 10–25 mCi each.

To allow convenient conversion from activity to exposure rate, a physical property termed "gamma factor", $\Gamma$, is conventionally employed, and tables of $\Gamma$ for various radioisotopes are available in the literature. This same property, $\Gamma$, is sometimes termed "specific gamma ray constant." The definition of $\Gamma$ is based on the model of a 1.0 mCi point source, with exposure rate measured in roentgen (R) units at a point 1.0 cm away. $\Gamma$ may be stated as roentgens per hour at a distance of 1.0 cm per mCi of source material. Specifically, the units for $\Gamma$ are $(R \cdot cm^2)/(hr \cdot mCi)$.

For purposes of comparison, the gamma factor, $\Gamma$, for cesium-137 is 3.32 $(R \cdot cm^2)/(hr \cdot mCi)$. $\Gamma$ for radium is 8.25 $(R \cdot cm^2)/(hr \cdot mCi)$.

The gamma factor, $\Gamma$, for americium-241 is relatively low, only 0.13 $(R \cdot cm^2)/(hr \cdot mCi)$. One making a conventional comparison, looking at $\Gamma$ alone, would at the outset see that at least $8.25/0.13 = 63$ times as much americium-241 as radium would be required to produce the same exposure tate (roentgens per hour) to a nearby point.

Moreover, americium-241 exhibits significant self-absorption to its own 60 keV gamma emission. As a result, its possible utility for therapeutic purposes is placed even further in doubt. Even with an exemplary source design employing a favorable geometry, self-absorption is calculated to be 88%, or, expressed alternatively, transmission of 12%. Therefore, rather than needing only 63 times as much americium-241 as radium, $63/0.12 = 525$ times as much americium-241 as radium would apparently be required to produce the same exposure rate.

Accordingly, one making this conventional comparison would reasonably conclude that americium-241 is a poor choice for at least the following reasons:

1. "Too much" activity would be required; and
2. Even so, there apparently still would not be enough, in a practical size, to produce an adequate exposure rate of approximately 20.0 R/hr.

Further, as a result of the relatively high activity (in curie amounts rather than millicurie amounts) required for an americium-241 source, a significant level of alpha radiation becomes an additional drawback. The main mode of americium-241 decay is by alpha emission at 5.5 MeV. Alpha particles comprise helium nuclei which decay by combining with free electrons to produce helium gas. Thus, a rigorously secure encapsulation, necessary with any brachytherapy source, is particularly required in order to safely contain the significant alpha emission, to withstand the resultant helium gas pressure buildup, and at the same time not unduly attenuate the desired gamma radiation.

Another potential drawback particularly arising from the alipha radiation is the potential for the production of neutrons resulting from bombardment of the capsule wall material with alpha particles. Neutrons show the potential of being beneficial for therapy, although the question is not settled. However, for present purposes thay are considered as introducing distracting complications, are it is accordingly assumed desirable to minimize the production of neutrons.

In accordance with the present invention, all of the foregoing considerations are effectively dealt with and the drawbacks overcome.

Concerning radiation output level and quantity considerations, there are two important aspects of the invention:

1. The self-absorption problem can be minimized through suitable geometric design, specifically, geometrical arrangements which provide a high surface area to volume ratio; and 2. Americium-241 has a previously unappreciated distinction over all previously-employed brachytherapy sources in that Compton scatter "buildup factors" in water or tissue increase the dose rate by 50% ($\times 1.5$) to nearby tissue compared to similar calculations for conventional sources. This is a function of the particular range of gamma ray energy involved (around 60 keV), and is a significant departure from the usual dose rate calculation. For all other brachytherapy isotopes the presence of water decreases the dose rate. While this effect has previously been analyzed in the general context of radiation therapy, it is of particularly great and previously unappreciated significance in an evaluation of americium-241 for the reason that taking this 50% increase into account means the difference between a conclusion that the radioisotope is quite advantageous and a conclusion that the radioisotope is apparently unsuitable.

In short, the additional 50% exposure rate makes it possible to achieve adequate dose rates where otherwise apparently only marginal dose rates could be achieved.

In accordance with the invention suitable sources may be constructed using available forms of americium-241 with activities up to 200 times greater than for radium sources of comparable size.

To relieve helium gas pressure buildup for long term use in therapeutic applications, it is recognized that a hollow cavity such as a hollow center in a generally cylindrical mass of americium-241 radioisotope may be provided. Further, as a matter of design choice, initial pressure within the cavity can be varied, and may be below atmospheric pressure. One alternative to such a hollow center contemplated by the invention is a loose mix of americium-241 powder. preferably with a binder, to provide a multiplicity of tiny reservoir spaces.

An encapsulation material which is satisfactory insofar as the requirement to transmit effective amounts of the low energy gamma radiation is titanium. In particular, a capsule wall having one or two titanium layers with a total thickness in the order of 1.0 millimeter is suitable.

Minimizing the production of neutrons can be accomplished through the selection of a capsule wall material having an atomic number sufficiently high to minimize neutron production, while at the same time not unduly attenuating low-energy gamma radiation. Titanium is a good compromise in this respect, and results in a neutron component of no more than approximately 1% of the total radiation dose.

Briefly stated, in a particular physical embodiment of the invention a radiation source for brachytherapy comprises a sealed capsule having a cavity, and a therapeutic quantity of americium-241 radioisotope disposed within the cavity. The capsule has walls of material and thickness selected to transmit therapeutically effective amounts of gamma radiation generated by the quantity of americium-241 radioisotope and to contain the quantity of americium-241 a radioisotope as well as to contain alpha particles and helium gas resulting from decay of alpha particles generated by the quantity of americium-241 radioisotope. While the particular embodiments disclosed herein have both single-layer and double-layer capsule walls of the same material, there is no intention to limit the invention to any particular number of layers, nor to the use of the same material for all layers.

The capsule wall material or materials preferably are also selected with a view to minimizing the production of neutrons by alpha bombardment, while at the same time transmitting therapeutically effective amounts of gamma radiation.

In order to alleviate helium gas pressure buildup, the capsule preferably includes a gas reservoir. Advantageously, the americium-241 comprises a cylindrical mass which provides the desirable property of increasing the surface area-to-volume ratio, as well as providing a convenient hollow reservoir for alleviating helium gas pressure buildup.

The americium-241 may comprise a variety of physical and chemical forms. However, the presently preferred form, and one which is commercially available, is americium-241 oxide powder. (Actually, both the oxide and dioxide forms are present but, for convenience, both are referred to herein as americium-241 oxide.)

Americium-241 is available in many other forms, such as a ceramic enamel. The amount of americium-241 which can be embedded in the ceramic enamel form is lower, however, than that contained in the americium-241 oxide powder. While the ceramic enamel form is safer when unencapsulated than the highly toxic powder form, with suitably designed containment the americium-241 oxide powder form is safe for use even in interstitially and intracavitary applications and, in fact, has a toxicity classification identical to that of the commonly used radium.

It is fully expected that other chemical and physical forms of americium-241 will be suitable in the radiotherapy application, as well as other encapsulation techniques. There is accordingly no intention to limit the scope of the claimed invention to the precise forms disclosed herein.

In accordance with the invention, a complete "kit" for americium-141 use may be provided, facilitating interstitial, intracavitary and surface applicator therapy. Such a kit includes quantities of suitably encapsulated americium-241 radioisotope in various shapes, applicators to contain the isotope in geometries suitable to the anatomical situation, and thin shields to serve either as partial radiation absorbers or full absorbers. These relatively thin radiation shields may be carried by, or used in close association with low energy gamma emitters to shield healthy tissue and allow a greater radiation dose to be delivered to malignant tissue than would otherwise be possible.

Briefly stated, and in accordance with another aspect of the invention, a method for radiation brachytherapy comprises temporarily placing a suitably contained quantity of americium-241 radioisotope at or near an affected region of a patient's body, thereby to expose the affected region to gamma radiation generated by the quantity of americium-241 radioisotope. The specific methods of application may be any of those presently known and/or employed, as it will be appreciated that some therapeutic effects as a result of the gamma radiation are readily predictable on the basis of prior experience with other low energy sources, for example, iodine-125. Additionally, it is appreciated that variations and improvements to known techniques, dosage distributions, dosage rates, and durations will continue to be developed, and there is accordingly no intention to limit the scope of the claimed invention to any particular technique or techniques.

Americium-241 is of course a well known radioisotope and has heretofore been employed for a number of purposes. For example, americium-241 is widely employed in ionization smoke detectors, such as is disclosed in the Ried, Jr. et al U.S. Pat. No. 4,044,263. Another radiation source employing americium-241 radioisotope is disclosed in the Dukes U.S. Pat. No. 3,488,502, which discloses a radioactive source capsule for radiation thickness gauges and the like. The disclosure of the Dukes U.S. Pat. No. 3,488,502 is of particular additional note for its recognition of and provisions for dealing with the problems of relatively high self attenuation and helium gas generation attendant to the use of americium-241.

Despite the relatively early (1970) date of the Dukes patent, as well as other uses of americium-241, the particular benefits of americium-141 for use in a radiotherapy source have heretofore gone unrecognized. As previously stated, the present invention recognizes that americium-241 has major advantages over radioisotopes previously employed for radiotherapy applications, which advantages far outweigh the problems which, as is demonstrated in accordance with the invention, are solveable in the radiotherapy, particularly brachytherapy, context.

Accordingly, it will be appreciated that the present invention provides an improved radiation source for brachytherapy, and the following four major advantages are listed by way of summary:

(1) Radiation Protection with Americium-241—Shielding problems are drastically simplified and are comparable to those involved in routine diagnostic radiology. For example, a 1.0 mm lead apron, which allows approximately 88% gamma transmission with cesium-137, allows less than 0.5% transmission for americium-241. For this reason, occupational exposures to brachytherapy personnel, currently among the highest in most hospitals, can be significantly reduced to levels comparable with diagnostic radiology. In addition, the substantial difficulties of radiation after-loading could be virtually eliminated.

(2) Dose Reduction to Healthy Tissue—With 60 keV gamma radiation, in-vivo shadow shielding is possible by a variety of techniques to protect healthy tissue from excessive radiation. In general, the shields required comprise thin high atomic number material, usually cladding or foils, and are positioned, whenever practicable, between the americium-241 source and the healthy tissue. One example is shielding the bladder and rectum during intracavitary cervical radiotherapy.

(3) Increased Dose to Tumor—Because of the ability to shield healthy tissue, americium-241 implants may be left in the patient for longer periods of time and, therefore, produce higher tumor doses. It has long been the experience in radiotherapy that higher tumor doses lead to higher cure rates, and the sources and techniques described herein in accordance with the invention offer the potential for this advantage.

(4) Improved Dose Distributions—Partially shielded sources can be used as compensators or wedges, sometimes in combination with other partially shielded sources, to provide advantageous dose distributions. Partially shielded sources may also produce "sharp isodose edges" for better dose distribution and allow a finer degree of definition of the treatment volume.

BRIEF DESCRIPTION OF THE DRAWINGS

While the novel features of the invention are set forth with particularity in the appended claims, the invention, both as to organization and content, will be better understood and appreciated from the following detailed description, taken in conjunction with the drawings, in which:

FIG. 7A is a longitudinal sectional view of a needle similar to that of FIG. 5A which further includes a shield to produce a 180° radiation shadow;

FIG. 7B is a section taken along line 7B—7B of FIG. 7A;

FIG. 8A is a longitudinal cross-sectional view of a flattened needle similar to that of 6A, but including a shield to provide a 180° radiation shadow;

FIG. 8B is a section taken along line 8B—8B of FIG. 8A;

FIG. 9A shows a shielded brachytherapy radiation source configured as a cervical plaque;

FIG. 9B is a side view of the FIG. 9A source;

FIG. 10A is a partially sectioned plan view of a brachytherapy radiation source configured as a wafer intended for use in combination with a separate applicator;

FIG. 10B is a side view of the FIG. 10A source; and

DESCRIPTION OF THE PREFERRED EMBODIMENTS

Drawing FIGS. 1A-3 are conceptual representations to illustrate, at the outset, typical dose rate calculations, and the special considerations which apply for americium-241 sources. The remaining FIGS. 4A-11 illustrate actual physical embodiments in accordance with the invention.

Preliminarily, it should be noted that equations for calculating the amount of radiation transmitted through an attenuating medium include factors of the general form $$Be^{-\mu x}, \tag{1}$$

where $\mu$ is the linear attenuation coefficient for the particular medium, x is the distance through the medium, and B is a gamma ray "build-up" factor to account for the effects of Compton-type scatter as photons traverse the medium. The actual value of a build-up factor for a particular medium depends both on the gamma ray energy and the distance, and may be defined as the ratio of the total absorbed dose at a point to the absorbed dose due to primary radiation alone at that point. For additional information, reference is hereby made to Loevinger, Robert, "Absorbed Dose from Interstitial and Intracavitary Sources," in "Afterloading in Radiotherapy," Proceedings of Conference in New York City (May 6-8, 1971) DHEW Publication (FDA) 72-8024, pp. 192-203.

As stated generally above, americium-241 strongly self-absorbs its own 60 keV gamma emission. Specifically, the linear attenuation coefficient, $\mu$, for americium-241 is 89.9/cm. By comparison, $\mu$ for titanium is 3.87/cm, and $\mu$ for water (or tissue) is only 0.2/cm. Accordingly, source configurations of high surface area to volume ratio are called for.

Build-up factors for 60 keV photons and distances of interest herein are 1.00 for americium-241, 1.32 for titanium, and 2.16 for water (or tissue).

Figure 1A:
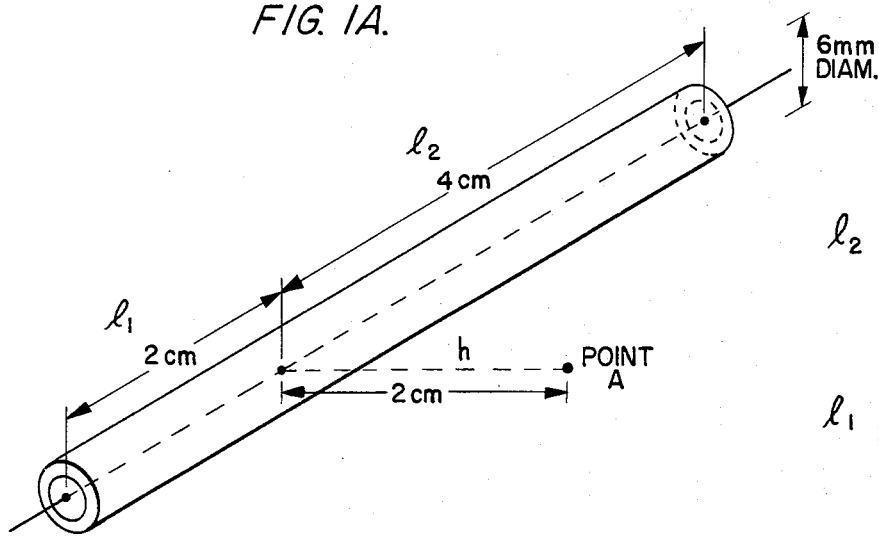
FIGS. 1A and 1B illustrate representative geometry for calculating dose rate to a Point A from a tandem.
Figure 1B:
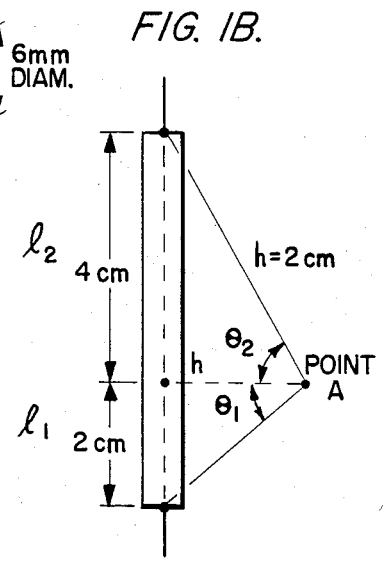

With particular reference now to representative FIGS. 1A and 1B, relevant geometry in a water medium is illustrated. Several americium-241 capsules, inserted into a cervical tandem, approximate a single, 6 cm long, tubular source. Point A is defined to be 2 cm "along" and 2 cm "away" from the lower edge of the tandem. Small amounts of Americium in the ends of each capsule are not included either in FIGS. 1A and 1B or in the dose rate calculation described below. Titanium encapsulation walls are for clarity omitted from FIGS. 1A and 1B. However, a 1.0 mm outer wall of titanium is considered in the calculation.

The dose rate at Point A from a tubular source distribution can be calculated using known equations. Only a small error (<5%) is made by assuming that all the 60 keV photon emission is concentrated at the axis of the The effect of self-absorption, however, is very significant to dose rates outside the source.

Figure 2:
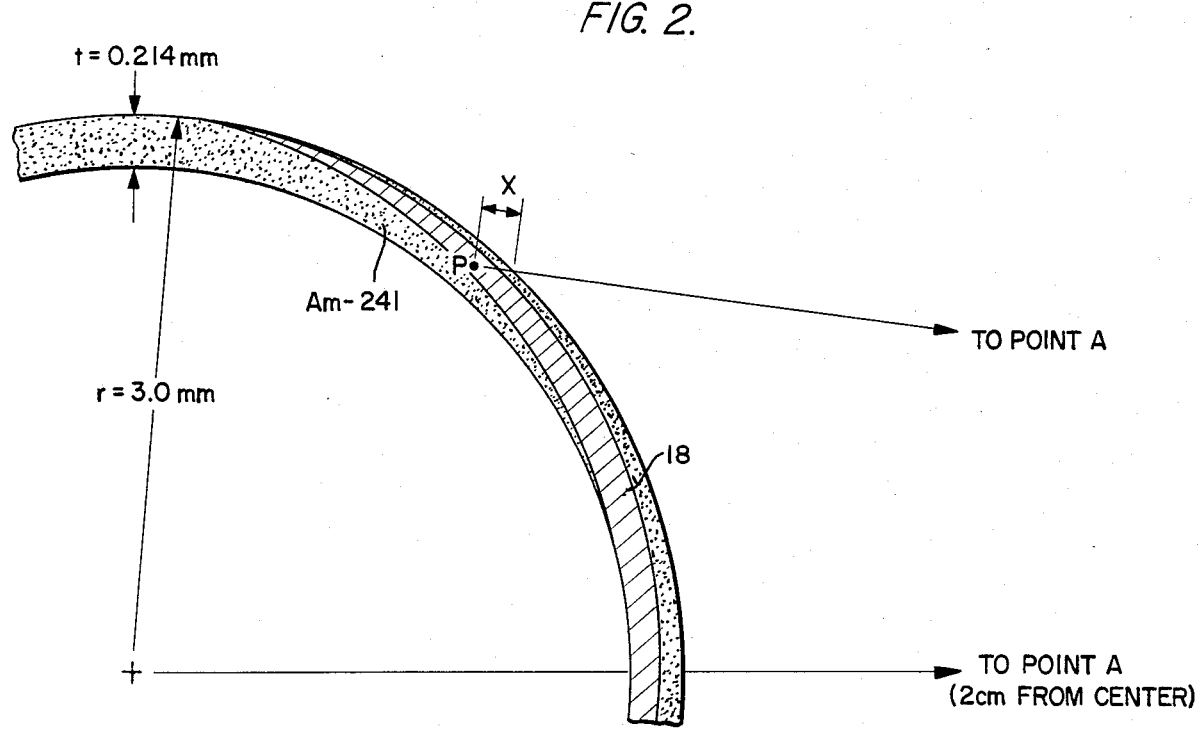
FIG. 2 is a greatly enlarged cross sectional view of the source of FIG. 1A to better illustrate the geometry.

FIG. 2 represents a cross-section of the americium-241 distribution. 7.8 Ci of americium are considered to be uniformly distributed in a band 0.214 mm thick and 6 cm long. The shaded area 18 represents an elementary strip whose center points, such as Point P, present a constant wall thickness X along a straight line to Point A. The activity contained in the volume defined by the strip is given by $A \cdot (m/M)$, where A is the total activity, m is the shaded strip area, and M is the total americium-241 cross-sectional area. The exposure rate dx/dt to Point A from each strip may be approximately expressed, assuming a 6 cm long filtered line source containing $A \cdot (m/M)$ Curies and having a wall thickness (of unradioactive americium) of x cm, by the following integral expression which accounts for the effect of oblique filtration along the line source:

$$\frac{dx}{dt} = \frac{A\left(\frac{m}{M}\right)\Gamma}{(l_1-l_2)h}\left\{\int_0^{\theta_1} e^{-\mu x \sec\theta}d\theta + \int_0^{\theta_2} e^{-\mu x \sec\theta}d\theta\right\} \tag{2}$$

where $l_1$, $l_2$, h, $\theta_1$ and $\theta_2$ are defined as shown in FIGS. 1A and 1B, with the expression $(l_1-l_2)$ being the total 6 cm length; $\Gamma$ is the gamma factor for Am-241, which is 0.13 (R·cm²)/(hr·mCi); and $\mu$ is the linear absorption coefficient for americium, which is 89.9/cm.

By then employing graphical integration techniques, the exposure rate in air (ignoring the water medium) has been calculated to be approximately 18.8 R/hr.

A similar calculation for an unfiltered line source yields a value of 159.3 R/hr. Thus, the transmission efficiency through americium is only $18.8/159.3 = 12\%$. Stated alternatively, the self-absorption is 88%.

The dose rate in units of Rads/hour in the water (or tisue) environment and with a titanium encapsulation is then calculated from the following equation:

$$\text{Dose Rate} = (\text{Exposure rate in air}) B_2 e^{-\mu_2 x_2} \cdot B_3 e^{-\mu_3 x_3} \cdot \bar{f} \tag{3}$$

where $B_2$ and $B_3$ are the build-up factors for titanium and water (or tissue), respectively; $\mu_2$ and $\mu_3$ are the linear attenuation coefficients for titanium and water (or tissue), respectively, $x_2$ and $x_3$ are the distances through titanium and water, respectively; and $\bar{f}$ is the Rads/R factor for the particular tissue to account for dose actually absorbed. For muscle, $\bar{f} = 0.93$ Rads/R.

For a 1.0 mm outer encapsulation, an "effective thickness" $x_2 = 0.117$ cm may be assumed. Then $$B_2 e^{-\mu_2 x_2} = 0.845 \tag{4}$$

For water, $x_3$ varies between 2.0 cm and 45 cm. The factor $$B_3 e^{-\mu_3 x_3} \tag{5}$$

correspondingly varies between 1.44 and 1.8. To simplify the calculation, a value of 1.5 is selected.

Substituting in equation (3):

$$\text{Dose Rate} = (18.8 \text{ R/hr})(0.845)(1.5)(0.93 \text{ Rads/R}) = 22.2 \text{ Rads/hr} \tag{6}$$

Some additional photons will emerge from the back half of the cylinder, undergo scatter in water, and then reach Point A. When the effect (estimated at 10% to 15%) is taken into consideration, the resultant Dose Rate becomes approximately 25 Rads/hr.

Thus, in the final dose rate calculation, water scatter adds 50% ($\times 1.5$) to the output. Assuming these calculations are correct, the additional 50% is crucial to the achieving of an adequate dose rate. (Approximately 20.0 R/hr is adequate.) This is not an obvious consideration that would normally be taken into account in a radioisotope selection process for the reason that the presence of water decreases the dose for all other brachytherapy isotopes.

Figure 3:
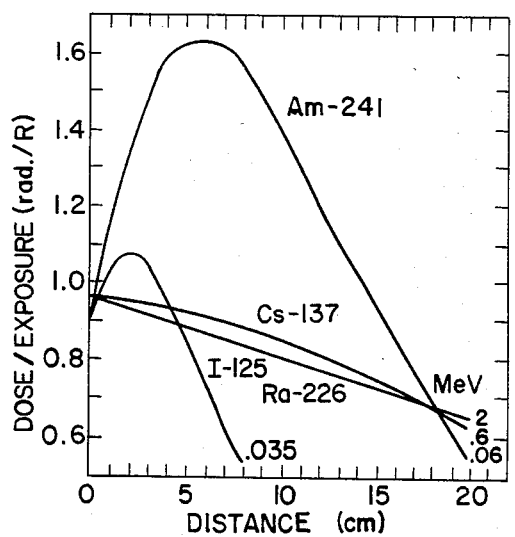
FIG. 3 is a a plot of dose per unit exposure versus distance for a point source of gamma radiation in water or tissue for various radioisotopes at various gamma ray energy levels.

This significant distinction of americium-241 over other radioisotopes depicted in FIG. 3 which is a graph plotting dose per unit exposure vs. distance for a point source of gamma radiation in water. The ordinates in FIG. 3 give the ratio of the absorbed dose to water at a given point to the exposure in air at the same point in the absence of water. These curves are taken from the Loevinger article, referenced above.

Specifically, for the 2.44 MeV gamma ray emission of Ra-226 and the 0.66 MeV gamma ray emission of Cs-137, the Compton scatter effects are not a significant factor. Even if they were, the precise dose rate calculation only would be affected, as the question whether output would be sufficient would not be involved.

In contrast, for the 0.06 MeV gamma ray emission of Am-241, the Compton scatter effects are significant at distances of interest, i.e., less than 10 cm.

For the 0.035 MeV gamma ray emission of I-125 there is some increase in absorbed dose due to Compton scatter effects, but the ratio is only slightly more than unity and it peaks at a distance of only 2.5 cm.

Figure 4A:
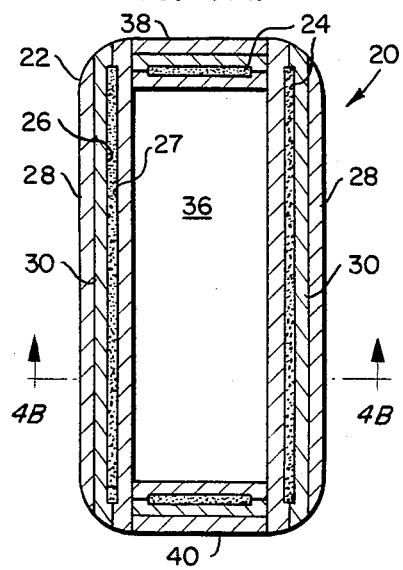
FIG. 4A is a longitudinal cross-sectional view of a generally cylindrical americium-241 capsule for brachytherapy.
Figure 4B:
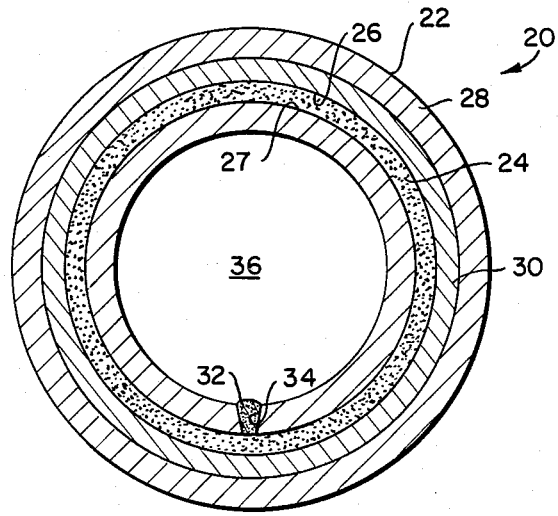
FIG. 4B is a cross-section taken along line 4B—4B of FIG. 4A.

With reference now to FIGS. 4A and 4B for an actual physical embodiment in accordance with the invention, a double encapsulated radiation source 20 for brachytherapy comprises a sealed capsule 22 with a therapeutic quantity 24 of americium-241 radioisotope distributed to fill a thin annular volume which effectively forms the shape of a cylindrical shell to increase the surface area-to-volume ratio. The radioisotope is encapsulated between outer and inner titanium walls 26 and 27, and may comprise compressed americium-241 oxide powder. The source 20 is double encapsulated in that the outer wall 26 in turn includes outer and inner layers 28 and 30 comprising titanium tubes, with all-welded construction. Each of the layers 28 and 30 has a thickness of 0.5 mm for an outer wall 26 overall thickness of 1.0 mm.

The nominal density of the quantity 24 of americium-241 is 11.1 curies/cm$^3$, and approximately 2.0 curies fill a 0.214 mm thick cylindrical shell.

At present, titanium appears to be the best choice for a wall material. In addition to great strength, the atomic number of titanium is low enough to allow the 60 keV photons to emerge from the source and simultaneously is high enough to avoid significant neutron generation (estimated less than 1%).

The inner layer 28 more particularly comprises a seamed tube with spot welds, such as at 32, spaced along a seam 34. A hollow-central volume 36 is thereby defined, which serves as a trap for helium gas pressure buildup. Helium enters the trap 36 through the seam 34 between the spot welds 32. Calculations of gas pressure build-up in this particular capsule indicate adequate wall strength for several hundred years. It will be appreciated that the initial pressure within the trap 36 may be varied as a matter of design choice, and may initially be less than atmospheric pressure.

End caps 38 and 40 (FIG. 4A) are of similar layered construction, and comprise disc-like members welded to the walls 26 and 28.

The cylindrical source 20 nominally has a 8.0 mm diameter and a 1.5 cm length. Such a source may be positioned into a 1.0 mm thick flexible plastic (Raphlex) tube to form a suitable tandem for GYN insertions. Although a smaller diameter might be clinically preferable, the larger dimension is necessary to maximize the surface/volume ratio of the americium-241 distribution to minimize the self-absorption that americium-241 has for its own 60 keV gamma emission.

The particular embodiment of FIGS. 4A and 4B has a specifically defined cavity (trap 36) for containing helium gas produced. It will be appreciated, however, that various alternatives are possible, and the invention is not limited to any particular such arrangement. For example, powdered americium-241 may be included in a mixture or binding not requiring a hollow center. A loose mix with adequate tiny reservoir spaces in between particles can provide sufficient sponge effect.

FIGS. 5A and 5B through 8A and 8B illustrate various forms of shielded and unshielded needles generally comprising americium-241 radioisotope material 42 within an outer shell 44 comprising a material with an intermediate atomic number, such as titanium. The outer shells have thicknesses in the order of 0.8 mm.

Figure 5A:
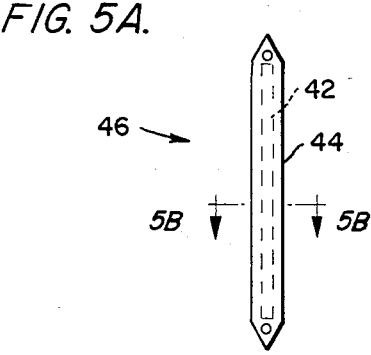
FIG. 5A is a longitudinal cross-sectional view of a brachytherapy source of circular needle configuration.
Figure 5B:
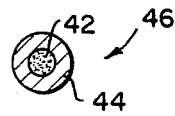
FIG. 5B is a section taken along line 5B—5B of FIG. 5A.

Specifically, FIGS. 5A and 5B illustrate a circular needle 46 with an overall length in the range of from 2.0 cm to 6.0 cm, and with a diameter in the range of from 0.1 cm to 0.3 cm.

Figure 6A:
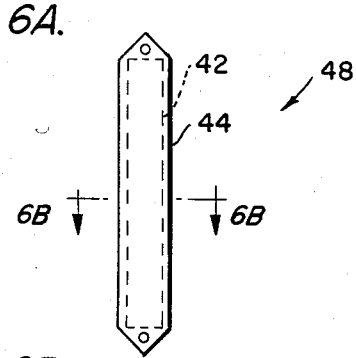
FIG. 6A is a longitudinal sectional view similar to that of FIG. 5A, showing a flattened needle.
Figure 6B:
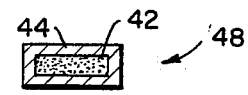
FIG. 6B is a sectional view taken along line 6B—6B of FIG. 6A.

FIGS. 6A and 6B illustrate a similarly sized flattened needle 48. The needle 48 may have a thickness in the range of from 0.1 cm to 0.3 cm, and a width in the range of from 0.2 cm to 0.9 cm.

FIGS. 7A and 7B illustrate a circular needle 50 and FIGS. 8A and 8B illustrate a flattened needle 52 which additionally include radiation shields 54 and 56 affixed to the outer shells 44 to produce a radiation shadow. A 180° shadow is typical, but other angles may be employed. The circular needle 50 also includes a plastic spacer 58 to preserve a cylindrical configuration, as may be seen from FIG. 7B.

FIGS. 9A and 9B illustrate the configuration of a cervical plaque 60 comprising an americium-241 disc 62 4.0 cm in diameter having titanium cladding 64 approximately 1.0 mm in thickness. Additionally, as may be seen in FIG. 9B, an external backshield 66 absorbs and attenuates rearward radiation, and may comprise a stainless steel or tungsten plate 0.2 cm in thickness. The FIG. 9B backshield 66 alternatively may be included within the cladding 64 in a manner similar to the illustration of FIG. 8B.

FIGS. 10A and 10B show the configuration a wafer 68 intend to fit a surface applicator. The wafer 68 comprises a body 70 of americium-241 material, with stainless steel or tungsten cladding 72 having a thickness in the order of 1.0 cm. The overall size of the wafer 68 of FIGS. 10A and 10B is as required to fit a surface applicator. The FIGS. 10A and 10B wafer 68 also may be provided with a backshield, either internal or external.

While various of the sources described hereinabove carry integral radiation shields, a variety of other shielding techniques are possible. In particular, separate, non-integral shields comprising thin high atomic number materials in the form of cladding or foils may be provided for positioning between the americium-241 source and healthy tissue. It is the low-energy gamma ray emission of americium-241 which makes this desirable result possible.

In accordance with the invention, a variety of such shields, together with various sizes and shapes of americium-241 capsules and chips, spacers, as well as applicators for various anatomical situations, are provided as a complete kit to cover a number of likely requirements.

Figure 11:
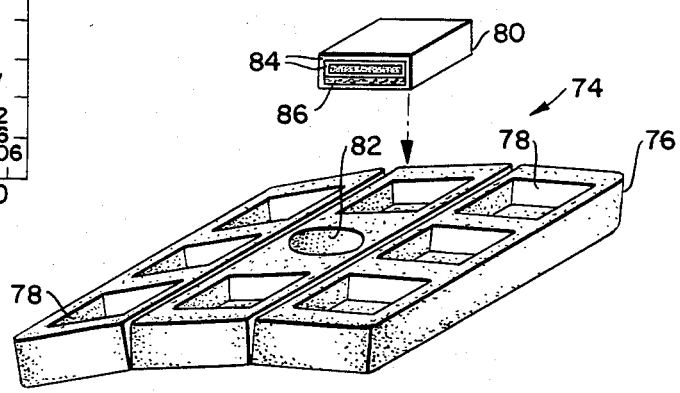
FIG. 11 is an overall view of a versatile americium-241 applicator and an exemplary wafer including an internal shield.

Finally FIG. 11 illustrates a configuration for an americium-241 applicator or "plaque" 74 suitable for delivering the ovoid portion of the GYN dose. The applicator 74 comprises a plastic or rubber holder 76 with a plurality of recesses 78 for receiving a plurality of 1 cm² thin planar "chips" of encapsulated americium-241, such as the representative chip 80. The holder 72 also has a central aperture 82 to allow clearance for a tandem. In this design, each chip 80 contains 600 mCi of americium-241 completely enclosed within double-welded 1.0 mm titanium cladding 84. A 1.0 mm thick tungsten shield 86 is built into the back of each chip 80, although the shield 86 may be carried on the outside. The shield 86 serves to confine the radiation to the forward direction, and protects both patient and medical personnel from unnecessary radiation (back-transmission < 1%).

The forward transmission efficiency of each americium chip 80 is estimated to be 44% and the dose rate to Point A, using calculations similar to those described above with reference to FIGS. 1A–3 is approximately 35 rads/hr. Thus, the total dose rate to Point A when tandem and plaque are used simultaneously, is 25+35=60 rads/hr.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A radiation source for brachytherapy consisting essentially of:
   a sealed capsule having a cavity therein; and
   a brachytherapeutically effective quantity of americium-241 radioisotope disposed within said cavity, wherein the walls of said capsule consist essentially of a material having a thickness which (1) will transmit brachytherapeutically effective dosages of gamma radiation generated by said quantity of americium-241 and, (2) will contain the helium gas resulting from the decay of the alpha particles generated by said quantity of americium-241, and (3) which provides a neutron component of no more than approximately 1% of the total radiation dose provided by said source.

2. A radiation source for brachytherapy according to claim 1 wherein said capsule wall consists essentially of titanium.

3. A radiation source for brachytherapy according to claim 1, wherein said quantity of americium-241 radioisotope is in the form of americium-241 oxide powder.

4. A radiation source for brachytherapy according to claim 1, wherein said quantity of americium-241 radioisotope is in the form of a ceramic enamel.

5. A radiation source for brachytherapy according to claim 1, wherein said capsule also includes a reservoir to alleviate helium gas pressure buildup.

6. A radiation source for brachytherapy according to claim 1, wherein said quantity of americium-241 radioisotope is provided in loosely-packed powder form with reservoir spaces between the particles thereof to alleviate helium gas pressure buildup.

7. A radiation source for brachytherapy according to claim 1, wherein said quantity of americium-241 radioisotope is in the form of a mass of cylindrical configuration.

8. A radiation source for brachytherapy according to claim 7, wherein a hollow reservoir is included within said cylindrical mass of americium-241 radioisotope to alleviate helium gas pressure buildup.

9. A radiation source for brachytherapy according to claim 1, wherein said capsule also includes a gamma-radiation shielding layer on a portion of said capsule to modify the gamma-radiation pattern provided by said course.

* * * * *